(12) United States Patent
Chan et al.

(10) Patent No.: US 7,361,821 B2
(45) Date of Patent: *Apr. 22, 2008

(54) CONTROLLED ALIGNMENT OF NANOBARCODES ENCODING SPECIFIC INFORMATION FOR SCANNING PROBE MICROSCOPY (SPM) READING

(75) Inventors: Selena Chan, Sunnyvale, CA (US); Xing Su, Cupertino, CA (US); Mineo Yamakawa, Campbell, CA (US)

(73) Assignee: Intel Corporation, Santa Clara, CA (US)

( * ) Notice: Subject to any disclaimer, the term of this patent is extended or adjusted under 35 U.S.C. 154(b) by 402 days.

This patent is subject to a terminal disclaimer.

(21) Appl. No.: 10/251,152

(22) Filed: Sep. 20, 2002

(65) Prior Publication Data

US 2004/0058328 A1 Mar. 25, 2004

(51) Int. Cl.
*C12Q 1/68* (2006.01)
*C12P 19/34* (2006.01)
*C07H 21/02* (2006.01)
*C07H 21/04* (2006.01)
*C07H 21/00* (2006.01)

(52) U.S. Cl. .................. 977/704; 977/728; 977/734; 977/742; 977/773; 977/774; 435/6; 435/91.1; 536/23.1; 536/24.3; 536/25.3

(58) Field of Classification Search .............. 435/6.71, 435/91.1, 183; 436/94; 536/23.1, 24.3, 536/25.3; 530/300, 350; 977/704, 728, 977/734, 742, 773, 774

See application file for complete search history.

(56) References Cited

U.S. PATENT DOCUMENTS

| | | | |
|---|---|---|---|
| 3,772,200 A | 11/1973 | Livesay | |
| 4,053,433 A | 10/1977 | Lee | 252/408 |
| 4,683,195 A | 7/1987 | Mullis | |
| 4,683,202 A | 7/1987 | Mullis | |
| 4,800,159 A | 1/1989 | Mullis | |
| 5,401,511 A | 3/1995 | Margalit | |
| 5,405,766 A | 4/1995 | Kallury | |
| 5,427,930 A * | 6/1995 | Birkenmeyer et al. | 435/91.52 |
| 5,451,505 A | 9/1995 | Dollinger | 435/6 |
| 5,472,881 A | 12/1995 | Beebe | |
| 5,538,898 A | 7/1996 | Wickramasinghe et al. | 436/94 |
| 5,603,872 A | 2/1997 | Margalit | |
| 5,610,287 A | 3/1997 | Nikiforov | |
| 5,620,854 A | 4/1997 | Holzrichter et al. | |
| 5,776,674 A | 7/1998 | Ulmer | |
| 5,840,862 A | 11/1998 | Bensimon et al. | |
| 5,986,076 A | 11/1999 | Rothschild | |
| 6,013,456 A | 1/2000 | Akhavan-Tafti | |
| 6,054,327 A | 4/2000 | Bensimon et al. | |
| 6,060,237 A * | 5/2000 | Nygren et al. | 435/6 |
| 6,187,823 B1 | 2/2001 | Haddon | |
| 6,225,055 B1 | 5/2001 | Bensimon et al. | |
| 6,225,068 B1 | 5/2001 | Wolfrum | |
| 6,248,537 B1 | 6/2001 | Bensimon et al. | |
| 6,258,401 B1 | 7/2001 | Crowley | |
| 6,265,153 B1 | 7/2001 | Bensimon et al. | |
| 6,280,939 B1 | 8/2001 | Allen | |
| 6,283,812 B1 | 9/2001 | Jin | |
| 6,297,592 B1 | 10/2001 | Goren | |
| 6,303,094 B1 | 10/2001 | Kusunoki et al. | |
| 6,303,296 B1 | 10/2001 | Bensimon et al. | |
| 6,319,670 B1 | 11/2001 | Sigal et al. | |
| 6,344,319 B1 | 2/2002 | Bensimon et al. | |
| 6,358,375 B1 | 3/2002 | Schwob | |
| 6,361,944 B1 * | 3/2002 | Mirkin et al. | 435/6 |
| 6,432,715 B1 | 8/2002 | Nelson et al. | 435/56 |
| 6,459,758 B1 | 10/2002 | Lee et al. | |
| 6,537,755 B1 | 3/2003 | Drmanac | 435/6 |
| 2002/0034827 A1 | 3/2002 | Singh et al. | |
| 2003/0148289 A1 | 8/2003 | Sundararajan et al. | |
| 2003/0165935 A1 * | 9/2003 | Vann et al. | 435/6 |

FOREIGN PATENT DOCUMENTS

WO    WO 92/15709    9/1992

(Continued)

OTHER PUBLICATIONS

Attached definition for "barcode".*

(Continued)

*Primary Examiner*—Frank Lu
(74) *Attorney, Agent, or Firm*—Darby & Darby, PC

(57) ABSTRACT

The methods, apparatus and compositions disclosed herein concern the detection, identification and/or sequencing of biomolecules, such as nucleic acids or proteins. In certain embodiments of the invention, coded probes comprising a probe molecule attached to one or more nanobarcodes may be allowed to bind to one or more target molecules. After binding and separation from unbound coded probes, the bound coded probes may be aligned on a surface and analyzed by scanning probe microscopy. The nanobarcodes may be any molecule or complex that is distinguishable by SPM, such as carbon nanotubes, fullerenes, submicrometer metallic barcodes, nanoparticles or quantum dots. Where the probes are oligonucleotides, adjacent coded probes hybridized to a target nucleic acid may be ligated together before alignment and SPM analysis. Compositions comprising coded probes are also disclosed herein. Systems for biomolecule analysis may comprise a scanning probe microscopy (SPM) instrument and at least one coded probe attached to a surface.

13 Claims, 4 Drawing Sheets

FOREIGN PATENT DOCUMENTS

| WO | WO97/15390 | 5/1997 |
|---|---|---|
| WO | WO 98/04740 | 2/1998 |
| WO | WO 00/29617 | 5/2000 |
| WO | WO 00/68692 | 11/2000 |
| WO | WO 01/25002 A1 | 4/2001 |
| WO | WO 02/32404 A2 | 4/2002 |

OTHER PUBLICATIONS

Blondel, et al., "Giant Magnetoresistance of Nanowires of Multilayers", *Am Inst of Phys*. 65(23):3018-3021, (Dec. 5, 1994).

Martin, et al., "Orthogonal Self-Assembly on Colloidal Gold-Platinum Nanorods", *Adv Mat*. 11(12)1021-1025, (1999).

Martin, Charles, "Membrane-Based Synthesis of Nanomaterials", *Chem. Mater*. 8:1739-1746, (1996).

Piraux, et al., "Giant Magnetorsistance in Magnetic Multilayered Nanowires", *Appl. Phys. Lett*. 65(19):2484-2486, (1994).

Boutorine, Alexandre S. et al., "Fullerene-Oligionucleotide Conjugates: Photo-Induced Sequence-Specific DNA Cleavage", *Angewandte Chemie*. 33(23/24):2462-2465, 1995.

Ando, Toshio, et al., "A High-Speed Atomic Force Microscope for Studying Biological Macromolecules," *PNAS*, vol. 98, No. 22, pp. 12468-12472, Oct. 2001.

Huang, Yu, et al., "Directed Assembly of One-Dimensional Nanostructures into Functional Networks," *Science*, vol. 291, pp. 630-633, Jan. 2001.

Ajdari, et al., "Free-flow Electrophoresis with Trapping by a Transverse Inhomogeneous Field," *Proc. Natl. Acad. Sci*., vol. 88, pp. 4468-4471, May 1991.

Ando, et al., "A High-Speed Atomic Force Microscope for Studying Biological Macromolecules," *PNAS*, vol. 98, No. 22, pp. 12468-12472, Oct. 2001.

Bensimon, et al., "Alignment and Sensitive Detection of DNA by a Moving Interface," *Science*, vol. 265, pp. 2096-2098, Sep. 1994.

Bensimon, et al, "Stretching DNA with a Receding Meniscus: Experiments and Models," *Physical Review Letters*, vol. 74, No. 23, pp. 4754-4757, Jun. 1995.

Clauss, et al., "Atomic Resolution STM Imaging of a Twisted Single-Wall Carbon Nanotube," *Physical Review B*, vol. 58, No. 8, pp. 4266-4269, Aug. 1998.

Clauss, et al., "Electron Backscattering on Single-Wall Carbon Nanotubes Observed by Scanning Tunneling Microscopy," *Europhys. Lett..*, 47(5), pp. 601-607, 1999.

Freitag, et al., "Local Electronic Properties of Single-Wall Nanotube Circuits Measured by Conducting-Tip AFM," *Physical Review B*, vol. 62, No. 4, pp. 2307-2310, Jul. 2000.

Frisbie, et al, "Functional Group Imaging by Chemical Force Microscopy," *Science*, vol. 265, pp. 2071-2074, Sep. 1994.

Gerdes, et al., "Combing a Carbon Nanotube on a Flat Metal-Insulator-Metal Nanojunction," *Europhys. Lett*., 48 (3), pp. 292-298, 1999. Retrieved from the Internet on Apr. 1, 2002: URL://<http://www.edpsciences.com/articles/euro/abs/1999/a48309/a48309.html> 1 page.

Herrick, et al., "Quantifying Single Gene Copy No. by Measuring Fluorescent Probe Lengths on Combed Genomic DNA," *PNAS*, vol. 97, No. 1, pp. 222-227, Jan. 2000.

Hirahara, et al., "One-Dimensional Metallofullerene Crystal Generated Inside Single-Walled Carbon Nanotubes," *Physical Review Letters*, vol. 85, No. 25, pp. 5384-5387, Dec. 2000.

Hu, et al., "Imaging of Single Extended DNA Molecules on Flat (Aminopropyl)triethoxysilane Mica by Atomic Force Microscopy," *Langmuir*, vol. 12, No. 7, pp. 1697-1700, Apr. 1996.

Huang, et al., "Directed Assembly of One-Dimensional Nanostructures into Functional Networks," *Science*, vol. 291, pp. 630-633, Jan. 2001.

Kaczorowski, et al., "Co-Operativity of Hexamer Ligation," *Gene*, 179, (1996), pp. 189-193.

Kim, et al., "AFM Study of Surface Phenomena Based on $C_{60}$ Film Growth," *Applied Surface Science*, 130-132, pp. 602-609, 1998.

Klein, et al., "Ordered Stretching of Single Molecules of Deoxyribose Nucleic Acid Between Microfabricated Polystyrene Lines," *Applied Physics Letters*, vol. 78, No. 16, pp. 2396-2398, Apr. 2001.

Kobayashi, et al., " Imaging of Fullerene Molecules on Si(111)-7 7 Surface with NC-AFM," *Applied Surface Science*, 157, pp. 228-232, 2000.

Kotler, et al., "DNA Sequencing: Modular Primers Assembled from a Library of Hexamers or Pentamers," *Proc. Natl. Acad. Sci*., vol. 90, pp. 4241-4245, May 1993.

Liu, et al., "Fullerene Pipes," *Science*, vol. 280, pp. 1253-1256, May 1998.

Michalet, et al., "Dynamic Molecular Combing: Stretching the Whole Human Genome for High-Resolution Studies," *Science*, vol. 277, pp. 1518-1523, Sep. 1997.

Nicewarmer-Peña, "Submicrometer Metallic Barcodes," *Science*, vol. 294, pp. 137-141, Oct. 2001.

Odom, et al., "Single-Walled Carbon Nanotubes," *Ann. N.Y. Acad. Sci*., 960: 203-215, (2002). Retrieved from the Internet on Jul. 2, 2002, URL://<http://annalsnyas.org/cgi/content/full/960/1/203> 10 pages.

Ondarçuhu, et al. "Parallel Fabrication and Electrical Characterisation of Carbon Nanotube Hybrid Molecular Devices," 2 pages, Oct. 2000.

Schoenfeld, et al., "Formation of Si Quantum Dots in Nanocrystalline Silicon," *Solid-State Electronics*, vol. 40, Nos. 1-8, pp. 605-608, 1996.

Uchihashi, et al, "Application of Noncontact-Mode Atomic Force Microscopy to Molecular Imaging," Retrieved from the Internet on Jul. 3, 2002, URL://<http://www.foresight.org/Conferences/MNT7/Abstracts/Uchihashi/> 2 pages.

Wildöer, et al., "Electronic Structure of Atomically Resolved Carbon Nanotubes," *Nature*, vol. 391, pp. 59-62, Jan. 1998.

Woolley, et al., "Direct Haplotyping of Kilobase-Size DNA Using Carbon Nanotube Probes," *Nature Biotechnology*, vol. 18, pp. 760-763, Jul. 2000.

Li, "Biological Applications of AFM," Retrieved from the Internet on Jul. 12, 2002, URL://<http://www.chembio.uoguelph.ca/educmat/chm729/afm/applicat.htm> 2 pages.

"Carbon Nanotubes," Retrieved from the Internet on Jul. 2, 2002, URL://<http://www.1rsm.upenn.edu/nanophysics/nanotubes.html> 2 pages.

Fischer, et al., "Carbon Nanotube-Derived Materials," Retrieved from the Internet on Jul. 12, 2002, URL://<http://www.1rsm.upenn.edu/1rsm/IRG_2.pdf> pp. 32-41.

Venema et al., "Imaging Electron Wave Functions of Quantized Energy Levels in Carbon Nanotubes," Los Alamos Physics Preprints:cond-mat/9811317, Nov. 23, 1996.

Attachment of Free Flow Electrophoresis. http://www.aesociety.org/areas/ffe1.php. Accessed Oct. 23, 2007.

* cited by examiner

CONTROLLED ALIGNMENT OF NANOBARCODES ENCODING SPECIFIC INFORMATION FOR SCANNING PROBE MICROSCOPY (SPM) READING

FIELD OF THE INVENTION

The present methods, compositions and apparatus relate to the fields of molecular biology and analysis of biomolecules including, but not limited to, nucleic acids, proteins, lipids and polysaccharides. In particular, the invention relates to methods, compositions and apparatus for detection, identification and/or sequencing of nucleic acids and/or other biomolecules using nanobarcodes and scanning probe microscopy (SPM).

BACKGROUND

Identification and/or sequencing of biomolecules, such as nucleic acids or proteins, is essential for medical diagnostics, forensics, toxicology, pathology, biological warfare, public health and numerous other fields. Although a great deal of research is presently directed towards identification and/or sequencing of nucleic acids or proteins, other biomolecules such as carbohydrates, polysaccharides, lipids, fatty acids, etc. may be of importance. The methods, compositions and apparatus disclosed herein are not limited to identification and/or sequencing of nucleic acids, but are also of use for analysis of other types of biomolecules, including but not limited to proteins, lipids and polysaccharides.

Standard methods for nucleic acid detection, such as Southern blotting or binding to nucleic acid chips, rely on hybridization of a fluorescent or radioactive probe molecule with a target nucleic acid molecule. Known methods for nucleic acid sequencing typically utilize either the Sanger dideoxy technique or hybridization to nucleic acid chips.

Oligonucleotide hybridization based assays are in wide use for detection of target nucleic acids. A probe oligonucleotide that is complementary in sequence to a target nucleic acid is attached to a fluorescent, radioactive or other moiety and allowed to hybridize to a nucleic acid through Watson-Crick base pair formation. Many variations on this technique are known. More recently, DNA chips have been designed that can contain hundreds or even thousands of oligonucleotide probes. Hybridization of a target nucleic acid to an oligonucleotide on a chip may be detected using fluorescence spectroscopy, radioactivity, etc. Problems with sensitivity and/or specificity may result from nucleic acid hybridization between sequences that are not precisely complementary. The presence of low levels of a target nucleic acid in a sample may not be detected.

Methods for Sanger dideoxy nucleic acid sequencing, based on detection of four-color fluorescent or radioactive nucleic acids that have been separated by size, are limited by the length of the nucleic acid that can be sequenced. Typically, only 500 to 1,000 bases of nucleic acid sequence can be determined at one time. Using current methods, determination of a complete gene sequence requires that many copies of the gene be produced, cut into overlapping fragments and sequenced, after which the overlapping DNA sequences may be assembled. This process is laborious, expensive, inefficient and time-consuming. It also typically requires the use of fluorescent or radioactive moieties, which can potentially pose safety and waste disposal problems. More recent methods for nucleic acid sequencing using hybridization to oligonucleotide chips may be used to infer short nucleic acid sequences or to detect the presence of a specific nucleic acid in a sample, but are not suited for identifying long nucleic acid sequences.

A variety of techniques are available for identification of proteins, polypeptides and peptides. Commonly, these involve binding and detection of antibodies that can recognize one or more epitopic domains on the protein. Although antibody-based identification of proteins is fairly rapid, such assays may occasionally show unacceptably high levels of false positive or false negative results, due to cross-reactivity of the antibody with different antigens, low antigenicity of the target analyte (leading to low sensitivity of the assay), nonspecific binding of antibody to various surfaces, etc. They also require the preparation of antibodies that can recognize an individual protein or peptide. As such, they are not suitable for the identification of novel proteins that have not previously been characterized.

A need exists for rapid, accurate and sensitive methods for detection, identification and/or sequencing of biomolecules, such as nucleic acids or proteins.

BRIEF DESCRIPTION OF THE DRAWINGS

The following drawings form part of the present specification and are included to further demonstrate certain aspects of the disclosed embodiments of the invention. The embodiments of the invention may be better understood by reference to one or more of these drawings in combination with the detailed description of specific embodiments presented herein.

DESCRIPTION OF ILLUSTRATIVE EMBODIMENTS

Figure 1:
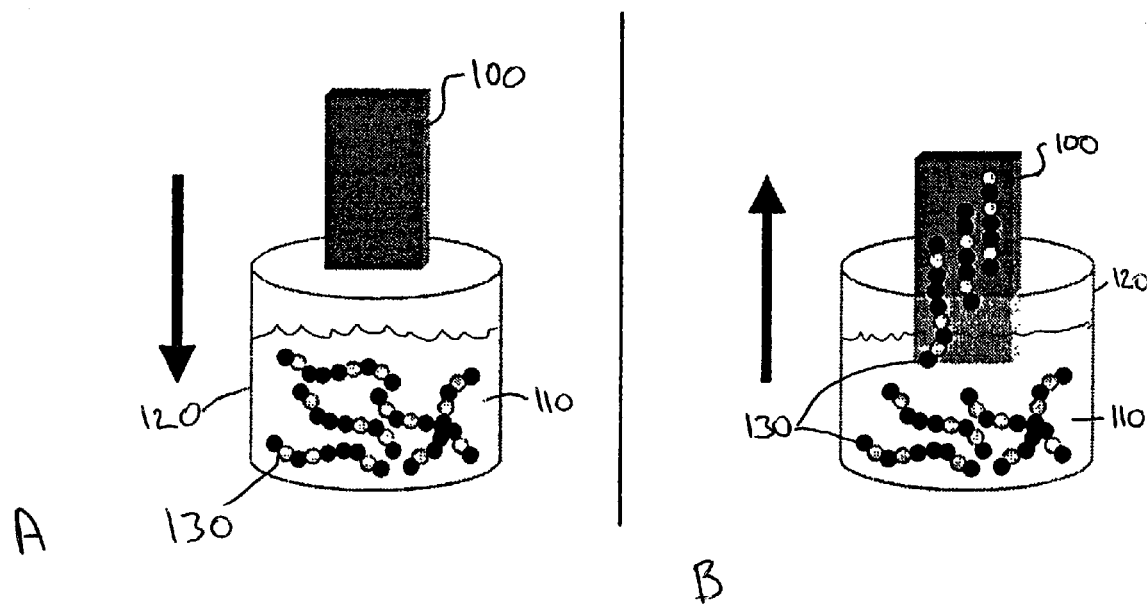
FIG. 1 illustrates an exemplary method for aligning coded probes 130, 230, 340, 400, each comprising one or more nanobarcodes 420 attached to a probe molecule 410, on a surface 100, 220, 300. (A) Immersion of a surface 100, 220, 300 into a solution 110 containing coded probes 130, 230, 340, 400. (B) Removal of the surface 100, 220, 300 containing aligned coded probes 130, 230, 340, 400 from solution 110.

The disclosed methods, compositions and apparatus are of use for detection, identification and/or sequencing of biomolecules, such as nucleic acids. In particular embodiments of the invention, the methods, compositions and apparatus are suitable for obtaining the sequences of very long nucleic acid molecules of greater than 1,000, greater than 2,000, greater than 5,000, greater than 10,000 greater than 20,000, greater than 50,000, greater than 100,000 or even more bases in length. Advantages include the ability to read long nucleic acid sequences in a single sequencing run, high speed of obtaining sequence data, low cost of sequencing and high efficiency in terms of the amount of operator time required per unit of sequence data. Other advantages include the sensitive and accurate detection and/or identification of nucleic acids, with low incidence of false positive results.

The following detailed description contains numerous specific details in order to provide a more thorough understanding of the disclosed embodiments of the invention. However, it will be apparent to those skilled in the art that the embodiments of the invention may be practiced without these specific details. In other instances, devices, methods, procedures, and individual components that are well known in the art have not been described in detail herein.

Definitions

As used herein, "a" or "an" may mean one or more than one of an item.

As used herein, "about" means within ten percent of a value. For example, "about 100" would mean a value between 90 and 110.

"Nucleic acid" encompasses DNA, RNA (ribonucleic acid), single-stranded, double-stranded or triple stranded and any chemical modifications thereof. Virtually any modification of the nucleic acid is contemplated. A "nucleic acid" may be of almost any length, from oligonucleotides of 2 or more bases up to a full-length chromosomal DNA molecule. Nucleic acids include, but are not limited to, oligonucleotides and polynucleotides.

"Coded probe" 130, 230, 340, 400 refers to a probe molecule 410 attached to one or more nanobarcodes 420. A probe molecule 410 is any molecule that exhibits selective and/or specific binding to one or more target molecules. In various embodiments of the invention, each different probe molecule 410 may be attached to a distinguishable nanobarcode 420, so that binding of a particular probe 410, from a population of different probe molecules 410, may be detected. The embodiments of the invention are not limited as to the type of probe molecules 410 that may be used. Any probe molecule 410 known in the art, including but not limited to oligonucleotides, nucleic acids, antibodies, antibody fragments, binding proteins, receptor proteins, peptides, lectins, substrates, inhibitors, activators, ligands, hormones, cytokines, etc. may be used. In certain embodiments of the invention, coded probes 130, 230, 340, 400 may comprise oligonucleotides and/or nucleic acids that have been covalently or non-covalently attached to one or more nanobarcodes 420 that identify the sequence of the oligonucleotide and/or nucleic acid. In various embodiments of the invention, a linear series of coded probes 130, 230, 340, 400 may be ligated together. Each coded probe 130, 230, 340, 400 in the ligated molecule may be attached to a distinguishable nanobarcode 420 to allow identification of its sequence. Since the sequence of coded probes 130, 230, 340, 400 in a ligated molecule may also be determined, the sequence of the entire ligated molecule may be identified. In alternative embodiments, each nucleotide within an oligonucleotide probe 410 may be attached to a distinguishable nanobarcode 420, allowing the sequence of the coded probe 130, 230, 340, 400 to be identified from the sequence of nucleotides.

Figure 4:
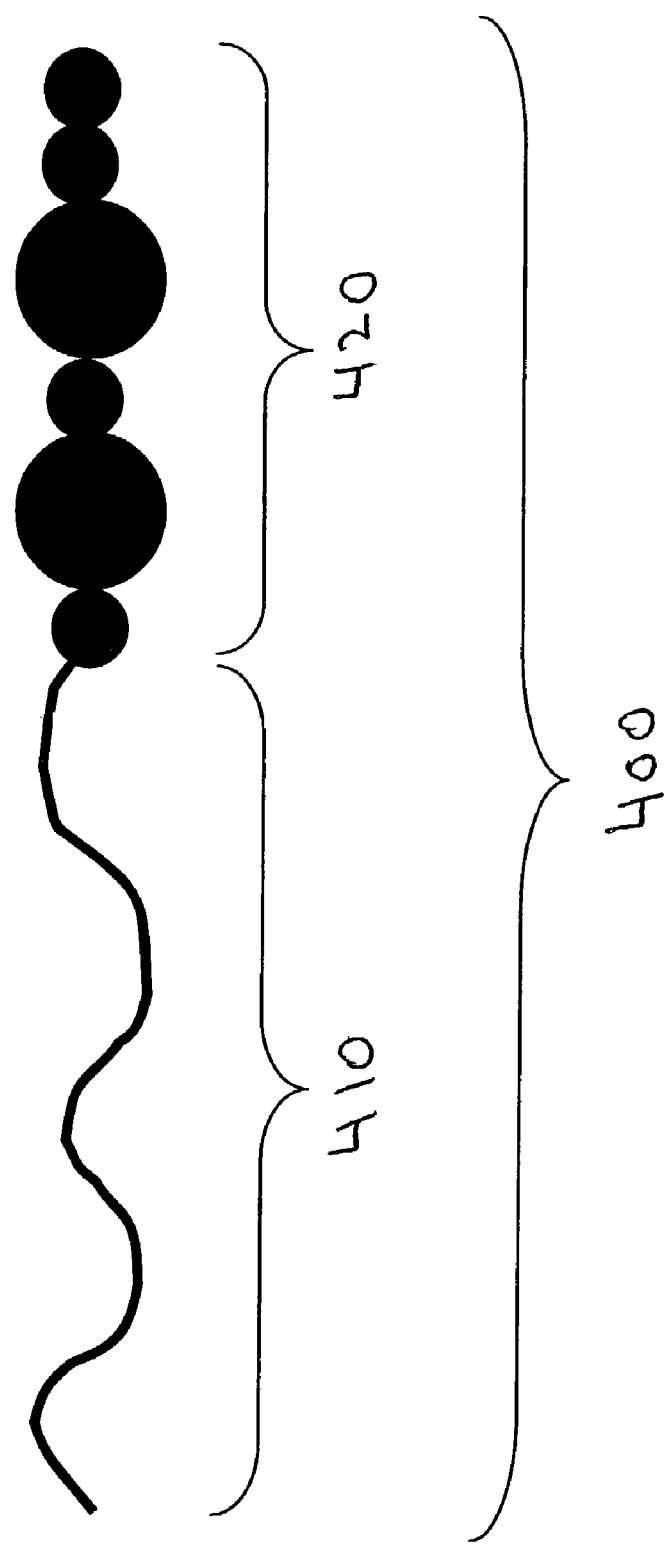
FIG. 4 illustrates an exemplary coded probe 400, comprising a nanobarcode 420 attached to a probe molecule 410. An individual nanobarcode 420 may be comprised of one or more moieties, as discussed in more detail below.

"Nanobarcode" 420 refers to a composition that may be used to detect and/or identify a coded probe 130, 230, 340, 400. In non-limiting examples discussed in more detail below, a nanobarcode 420 may comprise one or more submicrometer metallic barcodes, carbon nanotubes, fullerenes or any other nanoscale moiety that may be detected and identified by scanning probe microscopy. Nanobarcodes 420 are not limited to single moieties and in certain embodiments of the invention a nanobarcode 420 may comprise, for example, two or more fullerenes attached to each other. The non-limiting example illustrated in FIG. 4 shows six different moieties incorporated into a nanobarcode 420. Where the moieties are fullerenes, they may, for example, consist of a series of large and small fullerenes attached together in a specific order. The order of differently sized fullerenes in a nanobarcode 420 may be detected by scanning probe microscopy and used, for example, to identify the sequence of an attached oligonucleotide probe 410.

A "target" or "analyte" molecule is any molecule that may bind to a coded probe 130, 230, 340, 400, including but not limited to nucleic acids, proteins, lipids and polysaccharides. In some embodiments of the invention, binding of a coded probe 130, 230, 340, 400 to a target molecule may be used to detect the presence of the target molecule in a sample.

Molecular Combing

In various embodiments of the invention, nanobarcodes 420, coded probes 130, 230, 340, 400 and/or target molecules bound to coded probes 130, 230, 340, 400 may be attached to a surface 100, 220, 300 and aligned for analysis. In some embodiments, coded probes 130, 230, 340, 400 may be aligned on a surface and the incorporated nanobarcodes 420 detected as discussed below. In alternative embodiments, nanobarcodes 420 may be detached from the probe molecules 410, aligned on a surface and detected. In certain embodiments, the order of coded probes 130, 230, 340, 400 bound to an individual target molecule may be retained and detected, for example, by scanning probe microscopy. In other embodiments, multiple copies of a target molecule may be present in a sample and the identity and/or sequence of the target molecule may be determined by assembling all of the sequences of coded probes 130, 230, 340, 400 binding to the multiple copies into an overlapping target molecule sequence. Methods for assembling, for example, overlapping partial nucleic acid or protein sequences into a contiguous sequence are known in the art. In various embodiments, nanobarcodes 420 may be detected while they are attached to probe molecules 410, or may alternatively be detached from the probe molecules 410 before detection.

Methods and apparatus for attachment to surfaces 100, 220, 300 and alignment of molecules, such as nucleic acids, oligonucleotide probes 410 and/or nanobarcodes 420 are known in the art. (See, e.g., Bensimon et al., Phys. Rev. Lett. 74:4754-57, 1995; Michalet et al., Science 277:1518-23, 1997; U.S. Pat. Nos. 5,840,862; 6,054,327; 6,225,055; 6,248,537; 6,265,153; 6,303,296 and 6,344,319.) Nanobarcodes 420, coded probes 130, 230, 340, 400 and/or target molecules may be attached to a surface 100, 220, 300 and aligned using physical forces inherent in an air-water meniscus or other types of interfaces. This technique is generally known as molecular combing. Nanobarcodes 420, coded probes 130, 230, 340, 400 and/or target molecules dissolved in an aqueous medium 110, 210 may be attached at either one or both ends to a surface 100, 220, 300, such as a silanized glass slide, a biotinylated surface, a gold-coated surface or any other surface 100, 220, 300 known in the art capable of binding such molecules. The surface 100, 220, 300 may be slowly withdrawn from the aqueous medium (e.g., FIG. 1). Polar or charged target molecules, nanobarcodes 420, and/or coded probe molecules 130, 230, 340, 400 will preferentially partition into the hydrophilic (aqueous) medium 110, 210. Thus, removal of the surface 100, 220, 300 from the aqueous medium 110, 210 results in stretching of the bound target molecules, nanobarcodes 420 and/or coded probes 130, 230, 340, 400, parallel to the direction of movement of the meniscus. There is a direct correlation between the measured length of the stretched molecule and its actual size, with 1 m of stretched length corresponding to about 2,000 bases of nucleic acid sequence (Herrick et al., Proc. Natl. Acad. Sci. USA 97:222-227, 2000).

Once the surface 100, 220, 300 has been entirely removed from the aqueous medium 110, the attached nanobarcodes 420 and/or coded probes 130, 230, 340, 400 are aligned in a parallel fashion that may be more easily and accurately analyzed. In certain embodiments of the invention where both ends of a coded probe 130, 230, 340, 400 are attached to the surface 100, 220, 300, the aligned coded probes 130, 230, 340, 400 will be arranged in a U-shaped conformation that is also more easily analyzed. The technique is not limited by the size of the target molecules, nanobarcodes 420 and/or coded probes 130, 230, 340, 400 to be aligned, and can work on nucleic acids as long as whole chromosomes (e.g., Michalet et al., 1997; Herrick et al., 2000). At appropriate rates of movement of the meniscus the shear forces generated are relatively low, resulting in aligned DNA fragments of several hundred kilobases or longer (Michalet et al., 1997).

Molecular combing is inhibited by strong nonspecific adsorption of molecules to the treated surface 100, 220, 300 (Bensimon et al., 1995). Thus, in various embodiments of the invention, the surface 100, 220, 300 is treated so that only one or more ends of a target molecule or coded probe 130, 230, 340, 400 will bind to the surface 100, 220, 300. Methods for binding nucleic acids and other types of coded probes 130, 230, 340, 400 to surfaces 100, 220, 300 are well known in the art and are summarized below. In a non-limiting example, target molecules, nanobarcodes 420 or coded probes 130, 230, 340, 400 may be covalently modified with biotin residues at one or both ends of the molecule. Upon exposure to an avidin or streptavidin coated surface 100, 220, 300, only the biotinylated ends will bind to the surface 100, 220, 300. Nonspecific adsorption to a surface 100, 220, 300 may be decreased by the use of surfaces 100, 220, 300 that are hydrophobic in nature, such as silanized surfaces 100, 220, 300.

The embodiments of the invention are not limited by the type of surface 100, 220, 300 that may be used. Non-limiting examples of surfaces 100, 220, 300 include glass, functionalized glass, ceramic, plastic, polystyrene, polypropylene, polyethylene, polycarbonate, PTFE (polytetrafluoroethylene), PVP (polyvinylpyrrolidone), germanium, silicon, quartz, gallium arsenide, gold, silver, nylon, nitrocellulose or any other material known in the art that is capable of having target molecules, nanobarcodes 420 and/or coded probes 130, 230, 340, 400 attached to the surface 100, 220, 300. Attachment may be either by covalent or noncovalent interaction. Although in certain embodiments of the invention the surface 100, 220, 300 is in the form of a glass slide or cover slip, the shape of the surface 100, 220, 300 is not limiting and the surface 100, 220, 300 may be in any shape. In some embodiments of the invention, the surface 100, 220, 300 is planar.

Alternative methods for aligning target molecules, nanobarcodes 420 and/or coded probes 130, 230, 340, 400 on surfaces 100, 220, 300 are known in the art. (E.g., Bensimon et al., 1995; Michalet et al., 1997; U.S. Pat. Nos. 5,840,862; 6,054,327; 6,225,055; 6,248,537; 6,265,153; 6,303,296 and 6,344,319). It is contemplated that any known method of alignment may be used within the scope of the claimed subject matter. In certain embodiments of the invention, alignment occurs when target molecules, nanobarcodes 420 or coded probes 130, 230, 340, 400 dissolved in an aqueous medium 110, 210 are drawn through a moving meniscus. The mechanism by which the meniscus is moved is not important and may be accomplished, for example, by immersing a surface 100, 220, 300 in buffer solution 110, 210 and slowly withdrawing it from the solution 110, 210. Alternatively, a surface 100, 220, 300 may be immersed in a solution 10, 210 and the level of the meniscus may be slowly lowered by evaporation or by removal of liquid. In another alternative embodiment of the invention, a drop of solution 210 may be placed between a cover slip 200 and a surface 100, 220, 300, such as a glass slide. The surface 100, 220, 300 may be slowly pulled away from the cover slip 200. Because the solution 210 adheres to the cover slip 200, this results in the formation of an air-water interface at the edge where the cover slip 200 contacts the surface 100, 220, 300. Moving this interface aligns the target molecules, nanobarcodes 420 and/or coded probes 130, 230, 340, 400 on the surface 100, 220, 300. Another alternative method for aligning nanobarcodes 420 and/or coded probes 130, 230, 340, 400, discussed in more detail below, involves use of free-flow electrophoresis either in place of or during molecular combing.

Nucleic Acids

Nucleic acid molecules to be detected, identified and/or sequenced may be prepared by any technique known in the art. In certain embodiments of the invention, the nucleic acids are naturally occurring DNA or RNA molecules. Virtually any naturally occurring nucleic acid may be detected, identified and/or sequenced by the disclosed methods including, without limit, chromosomal, mitochondrial and chloroplast DNA and ribosomal, transfer, heterogeneous nuclear and messenger RNA. In some embodiments, the nucleic acids to be analyzed may be present in crude homogenates or extracts of cells, tissues or organs. In other embodiments, the nucleic acids may be partially or fully purified before analysis. In alternative embodiments, the nucleic acid molecules to be analyzed may be prepared by chemical synthesis or by a wide variety of nucleic acid amplification, replication and/or synthetic methods known in the art.

Methods for purifying various forms of cellular nucleic acids are known. (See, e.g., *Guide to Molecular Cloning Techniques*, eds. Berger and Kimmel, Academic Press, New York, N.Y., 1987; *Molecular Cloning: A Laboratory Manual*, 2nd Ed., eds. Sambrook, Fritsch and Maniatis, Cold Spring Harbor Press, Cold Spring Harbor, N.Y., 1989). The methods disclosed in the cited references are exemplary only and any variation known in the art may be used. In cases where single stranded DNA (ssDNA) is to be analyzed, ssDNA may be prepared from double stranded DNA (dsDNA) by any known method. Such methods may involve heating dsDNA and allowing the strands to separate, or may alternatively involve preparation of ssDNA from dsDNA by known amplification or replication methods, such as cloning into M13. Any such known method may be used to prepare ssDNA or ssRNA.

Although certain embodiments of the invention concern analysis of naturally occurring nucleic acids, virtually any type of nucleic acid could be used. For example, nucleic acids prepared by various amplification techniques, such as polymerase chain reaction (PCR™) amplification, could be analyzed. (See U.S. Pat. Nos. 4,683,195, 4,683,202 and 4,800,159.) Nucleic acids to be analyzed may alternatively be cloned in standard vectors, such as plasmids, cosmids, BACs (bacterial artificial chromosomes) or YACs (yeast artificial chromosomes). (See, e.g., Berger and Kimmel, 1987; Sambrook et al., 1989.) Nucleic acid inserts may be isolated from vector DNA, for example, by excision with appropriate restriction endonucleases, followed by agarose gel electrophoresis. Methods for isolation of nucleic acid inserts are known in the art. The disclosed methods are not limited as to the source of the nucleic acid to be analyzed and any type of nucleic acid, including prokaryotic, bacterial, viral, eukaryotic, mammalian and/or human may be analyzed within the scope of the claimed subject matter.

In various embodiments of the invention, multiple copies of a single nucleic acid may be analyzed by coded probe 130, 230, 340, 400 hybridization, as discussed below. Preparation of single nucleic acids and formation of multiple copies, for example by various amplification and/or replication methods, are known in the art. Alternatively, a single clone, such as a BAC, YAC, plasmid, virus, or other vector that contains a single nucleic acid insert may be isolated, grown up and the insert removed and purified for analysis. Methods for cloning and obtaining purified nucleic acid inserts are well known in the art.

The skilled artisan will realize that the scope of the claimed subject matter is not limited to analysis of nucleic acids, but also concerns analysis of other types of biomolecules, including but not limited to proteins, lipids and polysaccharides. Methods for preparing and/or purifying various types of biomolecules are known in the art and any such method may be used.

Coded Probe Libraries

In certain embodiments of the invention, coded probes 130, 230, 340, 400 may comprise a library of probe molecules 410, each different probe 410 attached to a distinguishable nanobarcode 420. Within a given library, it is possible that there may be more than one copy of a specific probe molecule 410. In this case, each copy of the same probe 410 would be attached to an identical nanobarcode 420. The types of probes 410 and nanobarcodes 420 used are not limiting and any known type of probe molecule 410, including but not limited to oligonucleotides, nucleic acids, antibodies, antibody fragments, binding proteins, receptor proteins, peptides, lectins, substrates, inhibitors, activators, ligands, hormones, cytokines, etc. may be used. Further, any type of distinguishable nanobarcode 420 may be used.

Oligonucleotide Libraries

In various embodiments of the invention, the coded probes 130, 230, 340, 400 may comprise oligonucleotide probes 410, such as oligonucleotides of defined sequence. The oligonucleotides 410 may be attached to distinguishable nanobarcodes 420, hybridized to a nucleic acid to be analyzed and adjacent coded probes 130, 230, 340, 400 ligated together. After separation from the nucleic acid, the ligated coded probes 130, 230, 340, 400 may be attached to a surface 100, 220, 300 and aligned, as discussed above. The aligned coded probes 130, 230, 340, 400 may then be analyzed by scanning probe microscopy (SPM). SPM analysis allows detection and identification of the nanobarcode 420 component of coded probes 130, 230, 340, 400 and determination of the sequence of coded probes 130, 230, 340, 400 binding to the nucleic acid. That information can be used to identify the nucleic acid and/or to determine the nucleic acid sequence. The skilled artisan will realize that the claimed subject matter is not limited to SPM detection methods, and any method of analysis that can detect and identify nanobarcodes 420 and/or coded probes 130, 230, 340, 400 aligned on a surface 100, 220, 300 may be used. The skilled artisan will also realize that SPM analysis is not limited to detection and identification of oligonucleotide-based coded probes 130, 230, 340, 400, but may be used with any type of coded probe 130, 230, 340, 400 and/or nanobarcode 420.

In alternative embodiments of the invention, coded probes 130, 230, 340, 400 may be detected without ligation of adjacent coded probes 130, 230, 340, 400. The coded probes 130, 230, 340, 400 may be hybridized to multiple copies of the same target molecule. Non-hybridized coded probes 130, 230, 340, 400 may be removed and the hybridized coded probes 130, 230, 340, 400 detected. In some embodiments, coded probes 130, 230, 340, 400 may be detected while still hybridized to target molecules. Alternatively, coded probes 130, 230, 340, 400 may be detached from the target molecules, for example by heating the sample, and then detected. In such embodiments, the nanobarcode 420 component may or may not be removed from the probe 410 component of the coded probes 130, 230, 340, 400 before detection.

In certain embodiments of the invention, coded probes 130, 230, 340, 400 may be detected while still attached to a target molecule. Given the relatively weak strength of the binding interaction between short oligonucleotide probes 410 and target nucleic acids, such methods may be more appropriate where, for example, coded probes 130, 230, 340, 400 have been covalently attached to the target molecule using cross-linking reagents, or where the binding interaction between probe molecule 410 and target is stronger, as with antibody-antigen interactions.

In various embodiments of the invention, oligonucleotide type coded probes 130, 230, 340, 400 may be DNA, RNA, or any analog thereof, such as peptide nucleic acid (PNA), which can be used to identify a specific complementary sequence in a nucleic acid. In certain embodiments of the invention one or more coded probe 130, 230, 340, 400 libraries may be prepared for hybridization to one or more nucleic acid molecules. For example, a set of coded probes 130, 230, 340, 400 containing all 4096 or about 2000 non-complementary 6 mers, or all 16,384 or about 8,000 non-complementary 7-mers may be used. If non-complementary subsets of oligonucleotide coded probes 130, 230, 340, 400 are to be used, a plurality of hybridizations and sequence analyses may be carried out and the results of the analyses merged into a single data set by computational methods. For example, if a library comprising only non-complementary 6-mers were used for hybridization and sequence analysis, a second hybridization and analysis using the same target nucleic acid molecule hybridized to those coded probe 130, 230, 340, 400 sequences excluded from the first library may be performed.

In some embodiments of the invention, the coded probe 130, 230, 340, 400 library may contain all possible sequences for a given oligonucleotide length (e.g., a six-mer library would consist of 4096 coded probes 130, 230, 340, 400). In such cases, certain coded probes 130, 230, 340, 400 will form hybrids with complementary coded probe 130, 230, 340, 400 sequences. Such hybrids, as well as unhybridized coded probes 130, 230, 340, 400, may be separated from coded probes 130, 230, 340, 400 hybridized to the target molecule using known methods, such as high performance liquid chromatography (HPLC), gel permeation chromatography, gel electrophoresis, ultrafiltration and/or hydroxylapatite chromatography. Methods for the selection and generation of complete sets or specific subsets of oligonucleotides of all possible sequences for a given length are known. In various embodiments, coded probes 130, 230,

340, 400 of 2, 3, 4, 5, 6, 7, 8, 9, 10, 11, 12, 13, 14, 15, 16, 17, 18, 19, 20, 21, 22, 23, 24, 25 or more nucleotides in length may be used.

In certain embodiments of the invention, the coded probe 130, 230, 340, 400 libraries may comprise a random nucleic acid sequence in the middle of the coded probe 130, 230, 340, 400 attached to constant nucleic acid sequences at one or both ends. For example, a subset of 12-mer coded probes 130, 230, 340, 400 could consist of a complete set of random 8-mer sequences attached to constant 2-mers at each end. These coded probe 130, 230, 340, 400 libraries can be subdivided according to their constant portions and hybridized separately to a nucleic acid, followed by analysis using the combined data of each different coded probe 130, 230, 340, 400 library to determine the nucleic acid sequence. The skilled artisan will realize that the number of sublibraries required is a function of the number of constant bases that are attached to the random sequences. An alternative embodiment may use multiple hybridizations and analyses with a single coded probe 130, 230, 340, 400 library containing a specific constant portion attached to random oligonucleotide sequences. For any given site on a nucleic acid, it is possible that multiple coded probes 130, 230, 340, 400 of different, but overlapping sequence could bind to that site in a slightly offset manner. Thus, using multiple hybridizations and analyses with a single library, a complete sequence of the nucleic acid could be obtained by compiling the overlapping, offset coded probe 130, 230, 340, 400 sequences.

In embodiments of the invention involving oligonucleotide libraries, oligonucleotides may be prepared by any known method, such as by synthesis on an Applied Biosystems 381A DNA synthesizer (Foster City, Calif.) or similar instruments. Alternatively, oligonucleotides can be purchased from a variety of vendors (e.g., Proligo, Boulder, Colo.; Midland Certified Reagents, Midland, Tex.). In embodiments where oligonucleotides are chemically synthesized, the nanobarcodes 420 may be covalently attached to one or more of the nucleotide precursors used for synthesis. Alternatively, the nanobarcode 420 may be attached after the oligonucleotide probe 410 has been synthesized. In other alternatives, the nanobarcode(s) 420 may be attached concurrently with oligonucleotide synthesis.

In certain embodiments of the invention, coded probes 130, 230, 340, 400 may comprise peptide nucleic acids (PNAs). PNAs are a polyamide type of DNA analog with monomeric units for adenine, guanine, thymine, and cytosine. PNAs are commercially available from companies such as PE Biosystems (Foster City, Calif.). Alternatively, PNA synthesis may be performed with 9-fluoroenyl-methoxycarbonyl (Fmoc) monomer activation and coupling using O-(7-azabenzotriazol-1-yl)-1,1,3,3-tetramethyluronium hexafluorophosphate (HATU) in the presence of a tertiary amine, N,N-diisopropylethylamine (DIEA). PNAs can be purified by reverse phase high performance liquid chromatography (RP-HPLC) and verified by matrix assisted laser desorption ionization—time of flight (MALDI-TOF) mass spectrometry analysis.

Nanobarcodes

Each coded probe 130, 230, 340, 400 may incorporate at least one covalently or non-covalently attached nanobarcode 420. The nanobarcodes 420 may be used to detect and/or identify individual coded probes 130, 230, 340, 400. In certain embodiments of the invention each coded probe 130, 230, 340, 400 may have two or more attached nanobarcodes 420, the combination of which is unique to a particular coded probe 130, 230, 340, 400. Combinations of nanobarcodes 420 can be used to expand the number of distinguishable nanobarcodes 420 available for specifically identifying a coded probe 130, 230, 340, 400 in a library. In other embodiments of the invention, the coded probes 130, 230, 340, 400 may each have a single unique nanobarcode 420 attached. The only requirement is that the signal detected from each coded probe 130, 230, 340, 400 must be capable of distinguishably identifying that coded probe 130, 230, 340, 400 from different coded probes 130, 230, 340, 400.

In certain embodiments of the invention, a nanobarcode 420 may be incorporated into a precursor prior to the synthesis of a coded probe 130, 230, 340, 400. For oligonucleotide-based coded probes 130, 230, 340, 400, internal amino-modifications for covalent attachment at adenine (A) and guanine (G) positions are contemplated. Internal attachment may also be performed at a thymine (T) position using a commercially available phosphoramidite. In some embodiments library segments with a propylamine linker at the A and G positions may be used to attach nanobarcodes 420 to coded probes 130, 230, 340, 400. The introduction of an internal aminoalkyl tail allows post-synthetic attachment of the nanobarcode 420. Linkers may be purchased from vendors such as Synthetic Genetics (San Diego, Calif.). In one embodiment of the invention, automatic coupling using the appropriate phosphoramidite derivative of the nanobarcode 420 is also contemplated. Such nanobarcodes 420 may be coupled to the 5'-terminus during oligonucleotide synthesis.

In general, nanobarcodes 420 will be covalently attached to the probe 410 in such a manner as to minimize steric hindrance with the nanobarcodes 420, in order to facilitate coded probe 130, 230, 340, 400 binding to a target molecule, such as hybridization to a nucleic acid. Linkers may be used that provide a degree of flexibility to the coded probe 130, 230, 340, 400. Homo-or hetero-bifunctional linkers are available from various commercial sources.

The point of attachment to an oligonucleotide base will vary with the base. While attachment at any position is possible, in certain embodiments attachment occurs at positions not involved in hydrogen bonding to the complementary base. Thus, for example, attachment can be to the 5 or 6 positions of pyrimidines such as uridine, cytosine and thymine. For purines such as adenine and guanine, the linkage is may be via the 8 position. The claimed methods and compositions are not limited to any particular type of probe molecule 410, such as oligonucleotides. Methods for attachment of nanobarcodes 420 to other types of probes 410, such as peptide, protein and/or antibody probes 410, are known in the art.

The embodiments of the invention are not limiting as to the type of nanobarcode 420 that may be used. It is contemplated that any type of nanobarcode 420 known in the art may be used. Non-limiting examples include carbon nanotubes, fullerenes and submicrometer metallic barcodes.

Metallic Barcodes

Examples of submicrometer metallic barcodes of potential use as nanobarcodes 420 are known in the art (e.g., Nicewarner-Pena et al., Science 294:137-141, 2001). Nicewarner-Pena et al. (2001) disclose methods of preparing multimetal microrods encoded with submicrometer stripes, comprised of different types of metal. This system allows for the production of a very large number of distinguishable nanbarcodes 420—up to 4160 using two types of metal and as many as $8 \times 10^5$ with three different types of metal. Such nanobarcodes 420 may be incorporated into coded probes 130, 230, 340, 400 and read by SPM technology. Methods of attaching metal particles, such as gold or silver, to oligonucleotide and other types of probe molecules 410 are known in the art (e.g., U.S. Pat. No. 5,472,881).

Carbon Nanotubes

Another exemplary nanobarcode 420 of use in the disclosed methods comprises single-walled carbon nanotubes (SWNTs). Nanotubes may be made in a variety of shapes and sizes that may be distinguished by SPM methods. (See, e.g., Freitag et al., Phys. Rev. B 62:R2307-R2310, 2000; Clauss et al., Europhys. Lett. 47:601-607, 1999; Clauss et al., Phys. Rev. B. 58:R4266-4269, 1998; Odom et al., Ann. N.Y. Acad. Sci. 960:203-215, 2002). Odom et al. (2002) disclose an STM (scanning tunneling microscope) technique that is capable of detecting discrete peaks in the tunneling spectra of SWNTs of 10 nm or less in size. Such peaks may represent van Hove singularities in the density of electronic states (DOS) of the carbon nanotubes.

The electronic properties of carbon nanotubes are modulated by the length and diameter of the tube. The sensitivity of the electronic wavefunction to length is illustrated by an estimate for the energy level splitting of a tube of length L.

$$\Delta E = h v_F / 2L \qquad (Eq. 1)$$

Where $h$ is Planck's constant and $v_F$ is the Fermi velocity ($8.1 \times 10^5$ m/sec) (Venema et al., "Imaging Electron Wave Functions of Carbon Nanotubes," Los Alamos Physics Preprints:cond-mat/9811317, 23 Nov. 1996.) The difference between electron energy levels is inversely proportional to the length of the nanotube, with finer splitting observed for longer tubes.

The optical properties of carbon nanotubes are also a function of tube diameter. The relationship between fundamental energy gap (highest occupied molecular orbital—lowest unoccupied molecular orbital) and tube diameter may be modeled by the following function.

$$E_{gap} = 2 y_0 a_{cc} / d \qquad (Eq. 2)$$

Where $y_0$ is the carbon-carbon tight bonding overlap energy (2.7±0.1 eV), $a_{cc}$ is the nearest neighbor carbon-carbon distance (0.142 nm) and d is the tube diameter (Jeroen et al., Nature 391:59-62, 1998).

For certain embodiments of the invention, nanotubes to be used as nanobarcodes 420 may have tube lengths of about 10 to 200 nm and a diameter of about 1.2 to 1.4 nm. The length or diameter of the nanotubes to be used as nanobarcodes 420 is not limited and nanotubes of virtually any length or diameter are contemplated It is contemplated that nanotubes may be prepared by known methods or obtained from commercial sources, for example, CarboLex (Lexington, Ky.), NanoLab (Watertown, Mass.), Materials and Electrochemical Research (Tucson, Ariz.) or Carbon Nano Technologies Inc. (Houston, Tex.). Some processing of either synthesized or purchased nanotubes may be appropriate before use. Processing may include purification of nanotubes from other contaminants, separation of nanotubes of mixed diameter and/or length into nanotubes of discrete diameter and length, removal of nanotube end caps and/or covalent modification to facilitate attachment of the nanotube to a probe 410 to form a coded probe 130, 230, 340, 400.

In certain embodiments of the invention, carbon nanotubes of varying length and/or diameter may be produced by a variety of techniques known in the art, including but not limited to carbon-arc discharge, chemical vapor deposition via catalytic pyrolysis of hydrocarbons, plasma assisted chemical vapor deposition, laser ablation of a catalytic metal-containing graphite target, or condensed-phase electrolysis. (See, e.g., U.S. Pat. Nos. 6,258,401, 6,283,812 and 6,297,592.) In some embodiments, nanotubes may be size sorted by mass spectrometry (See, Parker et al., J. Am. Chem. Soc. 113:7499-7503, 1991). Alternatively, nanotubes may be sorted using an AFM (atomic force microscope) or STM (scanning tunneling microscope) to precisely measure the geometry of individual nanotubes before incorporating them into coded probes 130, 230, 340, 400. Other methods of size fractionation known in the art, such as gas chromatography, time of flight mass spectrometry, ultrafiltration or equivalent techniques are contemplated. Once sorted, the carbon nanotubes may be derivatized and covalently attached to oligonucleotide probes 410 of known sequence or any other type of probe 410.

The minimum incremental change in tube length possible for a carbon nanotube is the length of the carbon-carbon bond, or about 0.142 nm. With a range of tube lengths of 200 nm, this would allow for about 1400 discrete nanobarcodes 420. However, the method is not limited to a single nanotube per coded probe 130, 230, 340, 400. In alternative embodiments, multiple nanotubes of different length and diameter may be attached to a single coded probe 130, 230, 340, 400. Using combinations of nanotubes of different length, the number of possible distinguishable nanobarcodes 420 increases exponentially. In some embodiments, a single nanotube may be attached to a single probe molecule 410 for simplicity of analysis.

Other embodiments of the invention concern methods of producing carbon nanotubes of defined length and diameter. In a non-limiting exemplary embodiment, a chip may contain a layer of SiC of preselected thickness, overlaying a layer composed, for example, of silicon or silicon doped with catalysts (e.g. metal atoms such as nickel). Using standard chip processing methods, such as photolithography and etching or laser ablation, the SiC layer may be divided into SiC deposits of any length, width, thickness and shape. Subsequently the chip may be heated under a vacuum, for example at about $10^{-7}$ Torr at about 1400° C., or alternatively from about $10^{-3}$ to $10^{-12}$ Torr, $10^{-4}$ to $10^{-10}$ Torr, or $10^{-5}$ to $10^{-9}$ Torr, and from 1200 to 2200° C. or 1400 to 2000° C. Under these conditions, SiC crystals spontaneously decompose and lose silicon atoms (U.S. Pat. No. 6,303,094). The remaining carbon atoms spontaneously assemble into carbon nanotubes. The size and shape of the SiC deposits may be precisely controlled to produce carbon nanotubes of any length and diameter.

The exemplary embodiments of the invention discussed above are not limiting and any method of producing carbon nanotubes of selected length and diameter may be used (e.g., U.S. Pat. Nos. 6,258,401; 6,283,812 and 6,297,592). In some embodiments, nanotube length may be adjusted by using a laser beam, electron beam, ion beam or gas plasma beam to trim the ends. Alternatively, the ends of the nanotubes could be brought into contact with a hot blade in an oxygen-containing atmosphere to oxidatively remove the ends of the tubes. A block containing the nanotubes could also be sectioned or polished to truncate the nanotubes.

In certain embodiments of the invention, carbon nanotubes may be derivatized with reactive groups to facilitate attachment to probe molecules 410. In a non-limiting example, nanotubes may be derivatized to contain carboxylic acid groups (U.S. Pat. No. 6,187,823). Carboxylate derivatized nanotubes may be attached to probe molecules 410 by standard chemistries, for example by carbodiimide mediated formation of an amide linkage with a primary or secondary amine group located on the probe 410. The methods of derivatization and cross-linking are not limiting and any reactive group or cross-linking methods known in the art may be used.

Fullerenes

In alternative embodiments of the invention, fullerenes may be used to as nanobarcodes 420. Methods of producing fullerenes are well known (e.g., U.S. Pat. No. 6,358,375). Fullerenes may be derivatized and attached to probe molecules 410 by methods similar to those disclosed above for carbon nanotubes. Fullerene-containing coded probes 130, 230, 340, 400 may be identified by SPM technologies, similar to those disclosed above for nanotubes.

In certain embodiments of the invention, fullerenes may be attached to individual nucleotides in an oligonucleotide coded probe 130, 230, 340, 400. In such case, only two different types of distinguishable fullerenes are required, as there are only four types of nucleotide found in an oligonucleotide and two types of fullerenes may be combined in four different combinations (e.g., AA, BB, AB and BA). Where individual nucleotides are attached to nanobarcodes 420, it may be appropriate to use known linking groups between the nucleotide and the fullerene to avoid steric hindrance with hybridization to target nucleic acids.

The skilled artisan will realize that nanobarcodes 420 of use in the disclosed methods are not limited to the embodiments disclosed herein, but may include any other type of known nanobarcode 420 that may be attached to a probe 410 and detected. Other non-limiting examples of nanobarcodes 420 of potential use include quantum dots (e.g., Schoenfeld, et al., Proc. 7th Int. Conf. on Modulated Semiconductor Structures, Madrid, pp. 605-608, 1995; Zhao, et al., 1st Int. Conf. on Low Dimensional Structures and Devices, Singapore, pp. 467-471, 1995). Quantum dots and other types of nanobarcodes 420 may be synthesized by known methods and/or obtained from commercial sources (e.g., Quantum Dot Corp., Hayward, Calif.). Other nanobarcodes 420 of potential use include nanoparticles, available, for example, from Nanoprobes Inc. (Yaphank, N.Y.) and Polysciences, Inc. (Warrington, Pa.).

Hybridization and Ligation of Oligonucleotide-Based Coded Probes

In various embodiments of the invention, hybridization of a target nucleic acid to an oligonucleotide-based coded probe 130, 230, 340, 400 library may occur under stringent conditions that only allow hybridization between fully complementary nucleic acid sequences. Low stringency hybridization is generally performed at 0.15 M to 0.9 M NaCl at a temperature range of 20° C. to 50° C. High stringency hybridization is generally performed at 0.02 M to 0.15 M NaCl at a temperature range of 50° C. to 70° C. It is understood that the temperature and/or ionic strength of an appropriate stringency are determined in part by the length of an oligonucleotide probe 410, the base content of the target sequences, and the presence of formamide, tetramethylammonium chloride or other solvents in the hybridization mixture. The ranges mentioned above are exemplary and the appropriate stringency for a particular hybridization reaction is often determined empirically by comparison to positive and/or negative controls. The person of ordinary skill in the art is able to routinely adjust hybridization conditions to allow for only stringent hybridization between exactly complementary nucleic acid sequences to occur.

Once short coded probes 130, 230, 340, 400 have been hybridized to a nucleic acid, adjacent coded probes 130, 230, 340, 400 may be ligated together using known methods (see, e.g., U.S. Pat. No. 6,013,456). Oligonucleotide sequences of as short as 6 to 8 bases may be efficiently hybridized to target nucleic acids (U.S. Pat. No. 6,013,456). Primer independent ligation may be accomplished using oligonucleotides of at least 6 to 8 bases in length (Kaczorowski and Szybalski, Gene 179:189-193, 1996; Kotler et al., Proc. Natl. Acad. Sci. USA 90:4241-45, 1993). Methods of ligating oligonucleotide coded probes 130, 230, 340, 400 that are hybridized to a nucleic acid template are known in the art (U.S. Pat. No. 6,013,456). Enzymatic ligation of adjacent oligonucleotide coded probes 130, 230, 340, 400 may utilize a DNA ligase, such as T4, T7 or Taq ligase or *E. coli* DNA ligase. Methods of enzymatic ligation are known (e.g., Sambrook et al., 1989).

Immobilization of Molecules

In various embodiments of the invention, the target molecules to be analyzed may be immobilized prior to, subsequent to and/or during coded probe 130, 230, 340, 400 binding. For example, target molecule immobilization may be used to facilitate separation of bound coded probes 130, 230, 340, 400 from unbound coded probes 130, 230, 340, 400. In certain embodiments, target molecule immobilization may also be used to separate bound coded probes 130, 230, 340, 400 from the target molecules before coded probe 130, 230, 340, 400 detection and/or identification. Although the following discussion is directed towards immobilization of nucleic acids, the skilled artisan will realize that methods of immobilizing various types of biomolecules are known in the art and may be used in the claimed methods.

Nucleic acid immobilization may be used, for example, to facilitate separation of target nucleic acids from ligated coded probes 130, 230, 340, 400 and from unhybridized coded probes 130, 230, 340, 400 or coded probes 130, 230, 340, 400 hybridized to each other. In a non-limiting example, target nucleic acids may be immobilized and allowed to hybridize to coded probes 130, 230, 340, 400, after which hybridized adjacent coded probes 130, 230, 340, 400 are ligated together. The substrate containing bound nucleic acids is extensively washed to remove unhybridized coded probes 130, 230, 340, 400 and coded probes 130, 230, 340, 400 hybridized to other coded probes 130, 230, 340, 400. Following washing, the hybridized and ligated coded probes 130, 230, 340, 400 may be removed from the immobilized target nucleic acids by heating to about 90 to 95° C. for several minutes. The ligated coded probes 130, 230, 340, 400 may be attached to a surface 100, 220, 300 and aligned by molecular combing, as disclosed above. The aligned coded probes 130, 230, 340, 400 may then be analyzed by SPM.

Immobilization of nucleic acids may be achieved by a variety of methods known in the art. In an exemplary embodiment of the invention, immobilization may be achieved by coating a substrate with streptavidin or avidin and the subsequent attachment of a biotinylated nucleic acid (Holmstrom et al., *Anal. Biochem.* 209:278-283, 1993). Immobilization may also occur by coating a silicon, glass or other substrate with poly-L-Lys (lysine), followed by covalent attachment of either amino- or sulfhydryl-modified nucleic acids using bifunctional crosslinking reagents (Running et al., *BioTechniques* 8:276-277, 1990; Newton et al., *Nucleic Acids Res.* 21:1155-62, 1993). Amine residues may be introduced onto a substrate through the use of aminosilane for cross-linking.

Immobilization may take place by direct covalent attachment of 5'-phosphorylated nucleic acids to chemically modified substrates (Rasmussen et al., *Anal. Biochem.* 198:138-142, 1991). The covalent bond between the nucleic acid and the substrate is formed by condensation with a water-soluble carbodiimide or other cross-linking reagent. This method facilitates a predominantly 5'-attachment of the nucleic acids via their 5'-phosphates. Exemplary modified substrates would include a glass slide or cover slip that has been treated in an acid bath, exposing SiOH groups on the glass (U.S. Pat. No. 5,840,862).

DNA is commonly bound to glass by first silanizing the glass substrate, then activating with carbodiimide or glutaraldehyde. Alternative procedures may use reagents such as 3-glycidoxypropyltrimethoxysilane (GOP), vinyl silane or aminopropyltrimethoxysilane (APTS) with DNA linked via amino linkers incorporated either at the 3' or 5' end of the molecule. DNA may be bound directly to membrane substrates using ultraviolet radiation. Other non-limiting examples of immobilization techniques for nucleic acids are disclosed in U.S. Pat. Nos. 5,610,287, 5,776,674 and 6,225,068. Commercially available substrates for nucleic acid binding are available, such as Covalink, Costar, Estapor, Bangs and Dynal. The skilled artisan will realize that the disclosed methods are not limited to immobilization of nucleic acids and are also of potential use, for example, to attach one or both ends of oligonucleotide coded probes 130, 230, 340, 400 to a substrate.

The type of substrate to be used for immobilization of the nucleic acid or other target molecule is not limiting. In various embodiments of the invention, the immobilization substrate may be magnetic beads, non-magnetic beads, a planar substrate or any other conformation of solid substrate comprising almost any material. Non-limiting examples of substrates that may be used include glass, silica, silicate, PDMS (poly dimethyl siloxane), silver or other metal coated substrates, nitrocellulose, nylon, activated quartz, activated glass, polyvinylidene difluoride (PVDF), polystyrene, polyacrylamide, other polymers such as poly(vinyl chloride) or poly(methyl methacrylate), and photopolymers which contain photoreactive species such as nitrenes, carbenes and ketyl radicals capable of forming covalent links with nucleic acid molecules (See U.S. Pat. Nos. 5,405,766 and 5,986,076).

Bifunctional cross-linking reagents may be of use in various embodiments of the invention. The bifunctional cross-linking reagents can be divided according to the specificity of their functional groups, e.g., amino, guanidino, indole, or carboxyl specific groups. Of these, reagents directed to free amino groups are popular because of their commercial availability, ease of synthesis and the mild reaction conditions under which they can be applied. Exemplary methods for cross-linking molecules are disclosed in U.S. Pat. Nos. 5,603,872 and 5,401,511. Cross-linking reagents include glutaraldehyde (GAD), bifunctional oxirane (OXR), ethylene glycol diglycidyl ether (EGDE), and carbodiimides, such as 1-ethyl-3-(3-dimethylaminopropyl) carbodiimide (EDC).

Scanning Probe Microscopy

Scanning probe microscopes (SPM) are a family of instruments that are used to measure the physical properties of objects on a micrometer and/or nanometer scale. Different modalities of SPM technology are available, discussed in more detail below. Any modality of SPM analysis may be used for coded probe 130, 230, 340, 400 detection and/or identification. In general, an SPM instrument uses a very small, pointed probe in very close proximity to a surface 100, 220, 300 to measure the properties of objects. In some types of SPM instruments, the probe may be mounted on a cantilever that may be a few hundred microns in length and between about 0.5 and 5.0 microns thick. Typically, the probe tip is raster-scanned across a surface 100, 220, 300 in an xy pattern to map localized variations in surface 100, 220, 300 properties. SPM methods of use for imaging biomolecules and/or detecting molecules of use as nanobarcodes 420 are known in the art (e.g., Wang et al., Amer. Chem.Soc. Lett., 12:1697-98. 1996; Kim et al., Appl. Surface Sci. 130, 230, 340-132:602-609, 1998; Kobayashi et al., Appl. Surface Sci. 157:228-32, 2000; Hirahara et al., Phys. Rev. Lett. 85:5384-87, 2000; Klein et al., Applied Phys. Lett. 78:2396-98, 2001; Huang et al., Science 291:630-33, 2001; Ando et al., Proc. Natl. Acad. Sci. USA 12468-72, 2001).

Scanning Tunneling Microscopy (STM)

Scanning tunneling microscopy was the first SPM technique developed in the early 1980's. STM relies on the existence of quantum mechanical electron tunneling between the probe tip and sample surface 100, 220, 300. The tip is sharpened to a single atom point and is raster scanned across the surface 100, 220, 300, maintaining a probe-surface 100, 220, 300 gap distance of a few angstroms without actually contacting the surface 100, 220, 300. A small electrical voltage difference (on the order of millivolts to a few volts) is applied between the probe tip and sample and the tunneling current between tip and sample is determined. As the tip scans across the surfaces 100, 220, 300, differences in the electrical and topographic properties of the sample cause variations in the amount of tunneling current. In certain embodiments of the invention, the relative height of the tip may be controlled by piezoelectric elements with feed-back control, interfaced with a computer. The computer can monitor the current intensity in real time and move the tip up or down to maintain a relatively constant current. In different embodiments, the height of the tip and/or current intensity may be processed by the computer to develop an image of the scanned surface 100, 220, 300.

Because STM measures the electrical properties of the sample as well as the sample topography, it is capable of distinguishing between different types of conductive material, such as different types of metal in a metal barcode. STM is also capable of measuring local electron density. Because the tunneling conductance is proportional to the local density of states (DOS), STM can also be used to distinguish carbon nanotubes that vary in their electronic properties depending on the diameter and length of the nanotube. STM may be used to detect and/or identify any nanobarcodes 420 that differ in their electrical properties.

An STM probe tip may be scanned across a surface 100, 220, 300 containing aligned coded probes 130, 230, 340, 400 to detect and identify each coded probe 130, 230, 340, 400 on the surface 100, 220, 300. Ligated coded probes 130, 230, 340, 400 may also be identified. Target molecules may be identified by determining which coded probes 130, 230, 340, 400 bind to the target molecule. In embodiments of the invention where the coded probes 130, 230, 340, 400 indicate the presence of specific sequences (such as oligonucleotide sequences), the sequence of the biomolecule may be determined from the sequence of the coded probes 130, 230, 340, 400 that bind to the target molecule.

Atomic Force Microscopy

Another modality of SPM is atomic force microscopy (AFM). Methods of biomolecule analysis by AFM are generally known in the art (e.g., Uchihashi et al., "Application of Noncontact-Mode Atomic Force Microscopy to Molecular Imaging," http://www.foresight.org/Conferences/MNT7/Abstracts/Uchihashi). In AFM microscopy, the probe is attached to a spring-loaded or flexible cantilever that is in contact with the surface 100, 220, 300 to be analyzed. Contact is made within the molecular force range (i.e., within the range of interaction of Van der Waal forces). Within AFM, different modes of operation are possible, including contact mode, non-contact mode and Tapping-Mode™.

In contact mode, the atomic force between probe tip and sample surface 100, 220, 300 is measured by keeping the tip-sample distance constant and measuring the deflection of the cantilever, typically by reflecting a laser off the cantilever onto a position sensitive detector. Cantilever deflection results in a change in position of the reflected laser beam. As in STM, the height of the probe tip may be computer controlled using piezoelectric elements with feedback control. In some embodiments of the invention a relatively constant degree of deflection is maintained by raising or lowering the probe tip. Because the probe tip may be in actual (Van der Waal) contact with the sample, contact mode AFM tends to deform non-rigid samples. In non-contact mode, the tip is maintained between about 50 to 150 angstrom above the sample surface 100, 220, 300 and the tip is oscillated. Van der Waals interactions between the tip and sample surface 100, 220, 300 are reflected in changes in the phase, amplitude or frequency of tip oscillation. The resolution achieved in non-contact mode is relatively low.

In TappingMode™, the cantilever is oscillated at or near its resonant frequency using piezoelectric elements. The AFM tip periodically contacts (taps) the sample surface 100, 220, 300, at a frequency of about 50,000 to 500,000 cycles per second in air and a lower frequency in liquids. As the tip begins to contact the sample surface 100, 220, 300, the amplitude of the oscillation decreases. Changes in amplitude are used to determine topographic properties of the sample. Because AFM analysis does not depend on electrical conductance, it may be used to analyze the topological properties of non-conductive materials. Certain types of nanobarcodes 420, including but not limited to carbon nanotubes, fullerenes and nanoparticles, that differ in their topological properties may be detected and/or identified by AFM techniques.

In alternative modes of AFM, additional information may be obtained besides the topological profile of the sample. For example, in lateral force microscopy (LFM), the probe is scanned perpendicular to its length and the degree of torsion of the cantilever is determined. Cantilever torsion will be dependent on the frictional characteristics of the surface 100, 220, 300. Since the frictional characteristics of coded probes 130, 230, 340, 400 may vary depending on their composition, LFM may be useful to detect and identify different coded probes 130, 230, 340, 400.

Another variation is chemical force microscopy (CFM), in which the probe tip is functionalized with a chemical species and scanned over a sample to detect adhesion forces between the chemical species and the sample (e.g., Frisbie et al., Science 265:2071-2074, 1994). Chemicals with differing affinities for nanobarcode 420 materials, such as gold or silver, may be incorporated into an AFM probe tip and scanned across a surface 100, 220, 300 to detect and identify nanobarcodes 420. Another SPM mode of potential use is force modulation imaging (Maivald et al., *Nanotechnology* 2:103, 1991). Uchihashi et al. (http://www.foresight.org/Conferences/MNT7/Abstracts/Uchihashi) disclose a method of biomolecule imaging using frequency modulation in non-contact mode AFM.

Other SPM modes that may potentially be used to detect and/or identify coded probes 130, 230, 340, 400 include magnetic force microscopy (MFM), high frequency MFM, magnetoresistive sensitivity mapping (MSM), electric force microscopy (EFM), scanning capacitance microscopy (SCM), scanning spreading resistance microscopy (SSRM), tunneling AFM and conductive AFM. In certain of these modalities, magnetic properties of a sample may be determined. The skilled artisan will realize that metal barcodes and other types of nanobarcodes 420 may be designed that are identifiable by their magnetic as well as by electrical properties.

SPM instruments of use for coded probe 130, 230, 340, 400 detection and/or identification are commercially available (e.g. Veeco Instruments, Inc., Plainview, N.Y.; Digital Instruments, Oakland, Calif.). Alternatively, custom designed SPM instruments may be used.

Information Processing and Control System and Data Analysis

In certain embodiments of the invention, a system for biomolecule analysis may comprise an information processing and control system. The embodiments are not limiting for the type of information processing system used. Such a system may be used to analyze data obtained from an SPM instrument and/or to control the movement of the SPM probe tip, the modality of SPM imaging used and the precise technique by which SPM data is obtained. An exemplary information processing system may incorporate a computer comprising a bus for communicating information and a processor for processing information. In one embodiment, the processor is selected from the Pentium® family of processors, including without limitation the Pentium® II family, the Pentium® III family and the Pentium® 4 family of processors available from Intel Corp. (Santa Clara, Calif.). In alternative embodiments of the invention, the processor may be a Celeron®, an Itanium®, an X-Scale® or a Pentium Xeon® processor (Intel Corp., Santa Clara, Calif.). In various other embodiments of the invention, the processor may be based on Intel® architecture, such as Intel® IA-32 or Intel® IA-64 architecture. Alternatively, other processors may be used.

The computer may further comprise a random access memory (RAM) or other dynamic storage device, a read only memory (ROM) or other static storage and a data storage device such as a magnetic disk or optical disc and its corresponding drive. The information processing system may also comprise other peripheral devices known in the art, such a display device (e.g., cathode ray tube or Liquid Crystal Display), an alphanumeric input device (e.g., keyboard), a cursor control device (e.g., mouse, trackball, or cursor direction keys) and a communication device (e.g., modem, network interface card, or interface device used for coupling to Ethernet, token ring, or other types of networks).

In particular embodiments of the invention, an SPM (scanning probe microscopy) unit may be connected to the information processing system. Data from the SPM may be processed by the processor and data stored in the main memory. The processor may analyze the data from the SPM to identify and/or determine the sequences of coded probes 130, 230, 340, 400 attached to a surface 100, 220, 300. By overlapping sequences of ligated coded probes 130, 230, 340, 400, the computer may compile a sequence of a target nucleic acid. Alternatively, the computer may identify different known biomolecule species present in a sample, based on the identities of coded probes 130, 230, 340, 400 attached to the surface 100, 220, 300.

It is appreciated that a differently equipped information processing system may be used for certain implementations. Therefore, the configuration of the system may vary in different embodiments of the invention. While the processes described herein may be performed under the control of a programmed processor, in alternative embodiments of the invention, the processes may be fully or partially implemented by any programmable or hardcoded logic, such as Field Programmable Gate Arrays (FPGAs), TTL logic, or Application Specific Integrated Circuits (ASICs), for example. Additionally, the disclosed methods may be performed by any combination of programmed general purpose computer components and/or custom hardware components.

In certain embodiments of the invention, custom designed software packages may be used to analyze the data obtained from an SPM. In alternative embodiments of the invention, data analysis may be performed, using an information processing system and publicly available software packages. Non-limiting examples of available software for DNA sequence analysis include the PRISM™ DNA Sequencing Analysis Software (Applied Biosystems, Foster City, Calif.), the Sequencher™ package (Gene Codes, Ann Arbor, Mich.), and a variety of software packages available through the National Biotechnology Information Facility at website www.nbif.org/links/1.4.1.php.

EXAMPLES

Example 1

Nanobarcodes and Scanning Probe Microscopy

Exemplary embodiments of the invention are illustrated in FIG. 1 through FIG. 4. FIG. 1A and FIG. 1B illustrate a non-limiting method for aligning coded probes 130, 230, 340, 400 on a surface 100, 220, 300. A surface 100, 220, 300, for example a glass microscope slide 100, 220, 300 that has been coated with streptavidin by known methods, is immersed in a solution 110, 210 containing biotinylated coded probes 130, 230, 340, 400.

The solution may be contained in a container 120.

In a non-limiting example, the coded probes 130, 230, 340, 400 comprise oligonucleotide probes 410 that have been hybridized to a target nucleic acid molecule. The nucleic acid molecule may be immobilized by attachment to a nylon membrane, 96-well microtiter plate or other immobilization substrate. Biotinylated oligonucleotides comprising, for example, all 4096 possible 6-mer sequences may be obtained from commercial sources (e.g., Midland Certified Reagents, Midland, Tex.). The biotinylated oligonucleotides may be attached, for example, to submicrometer metallic barcodes (Nicewarner-Pena et al., 2001) to form coded probes 130, 230, 340, 400. The coded probes 130, 230, 340, 400 are allowed to hybridize to a target nucleic acid. After hybridization, adjacent coded probes 130, 230, 340, 400 are ligated together using ligase. Unhybridized coded probes 130, 230, 340, 400 and coded probes 130, 230, 340, 400 hybridized to each other are removed by extensive washing, leaving only coded probes 130, 230, 340, 400 that are hybridized to the nucleic acid. The coded probes 130, 230, 340, 400 are removed by heating the solution 110, 210 to 95° C. for five minutes. The nucleic acid attached to the immobilization substrate is removed, leaving only ligated coded probes 130, 230, 340, 400 in solution 110, 210.

The biotinylated coded probes 130, 230, 340, 400 attach at one end to the streptavidin coated surface 100, 220, 300. The surface 100, 220, 300 is slowly removed from the solution 110, 210. Alternatively, liquid from the solution 110, 210 is slowly removed from the container 120, for example by evaporation or slow pumping. As the meniscus of the air-water interface slowly moves across the surface 100, 220, 300, the attached coded probes 130, 230, 340, 400 are aligned on the surface 100, 220, 300. The aligned coded probes 130, 230, 340, 400 may be analyzed by AFM, STM or other scanning probe methods.

Figure 2:
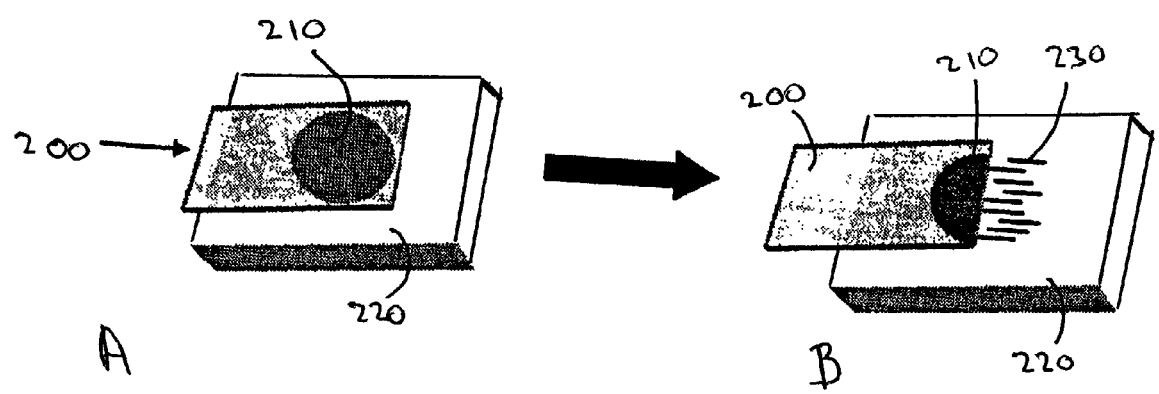
FIG. 2 illustrates an alternative exemplary method for aligning coded probes 130, 230, 340, 400 on a surface 100, 220, 300. (A) A drop of solution 210 containing coded probes 130, 230, 340, 400 is sandwiched between a cover slip 200 and a glass slide 220. (B) While the cover slip 200 is held in place, the slide 220 is moved, resulting in alignment of the coded probes 130, 230, 340, 400.

Another exemplary embodiment of the invention is illustrated in FIG. 2. A drop of solution 210 containing coded probes 130, 230, 340, 400 is placed on a surface 100, 220, 300, such as a glass slide. In certain embodiments, the slide 100, 220, 300 may be treated as disclosed above to bind one or both ends of the coded probes 130, 230, 340, 400. The drop 210 is sandwiched between the surface 100, 220, 300 and a glass cover slip 200. In various embodiments, the cover slip 200 may be held in a constant position while the surface 100, 220, 300 is slowly pulled away from the cover slip 200. This creates a meniscus at the edge of the cover slip 200 that serves to align the coded probes 130, 230, 340, 400.

In various embodiments of the invention, the coded probes 130, 230, 340, 400 may be attached to a surface 100, 220, 300 at both ends rather than at one end. In this case, alignment of the coded probes 130, 230, 340, 400 would result in a U-shaped molecule, instead of a linearized molecule (e.g. U.S. Pat. No. 5,840,862). The exemplary embodiments illustrated in FIG. 1 and FIG. 2 can also be performed by attaching both ends of the coded probes 130, 230, 340, 400 to the surface 100, 220, 300 (not shown).

Figure 3:
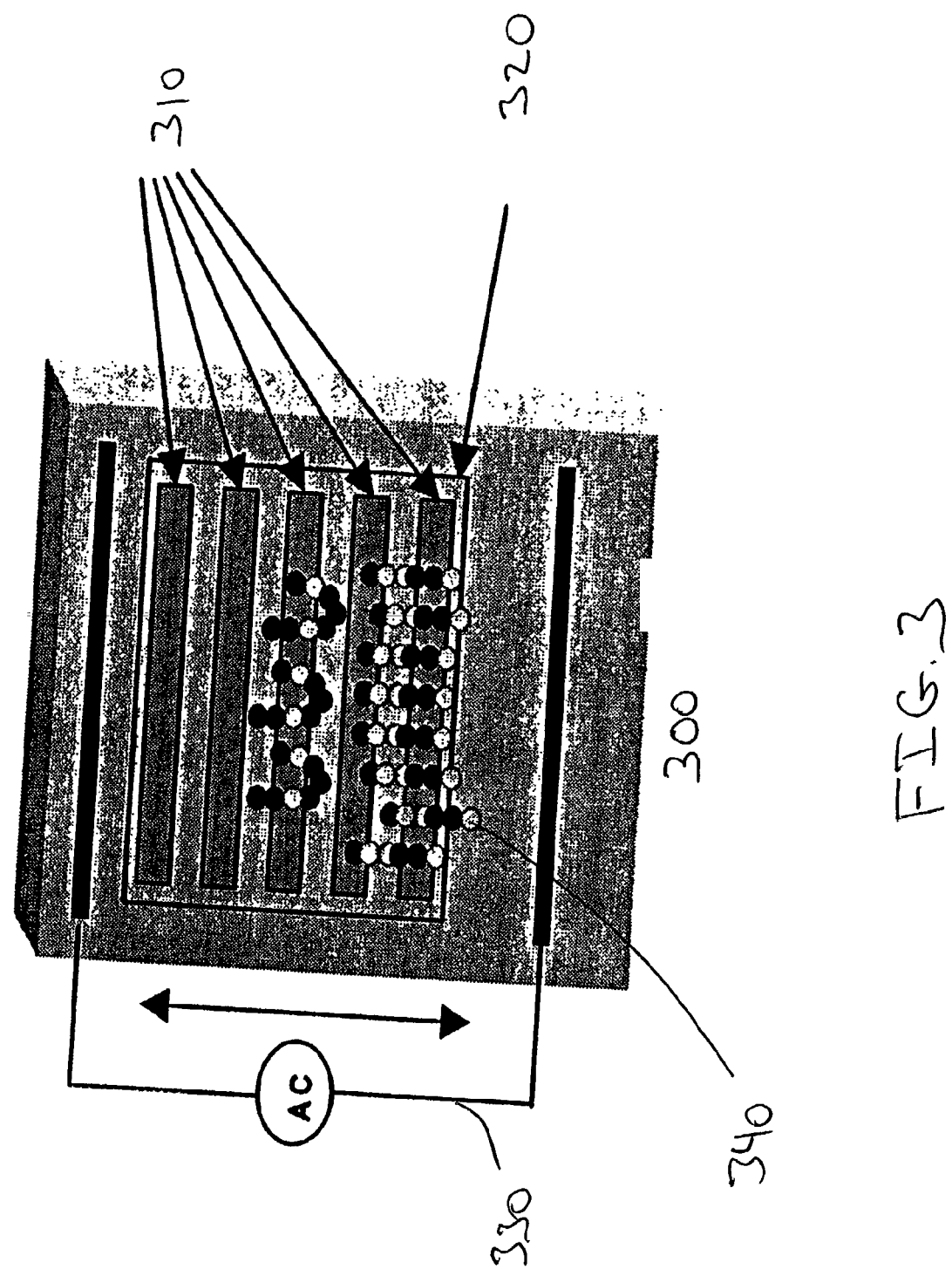
FIG. 3 illustrates another alternative exemplary method for aligning coded probes 130, 230, 340, 400 on a surface 100, 220, 300.

In another exemplary embodiment, illustrated in FIG. 3, coded probes 130, 230, 340, 400 may be aligned on a surface 100, 220, 300 by free flow electrophoresis. The surface may comprise alternating bands of conductive and non-conductive materials, such as a gold film 310 coated onto a glass sheet 320. In the presence of an alternating current electrical field 330, coded probes 130, 230, 340, 400 comprising charged residues, such as the phosphate groups on oligonucleotides, will align with the field 330. Free flow electrophoresis may be used in addition to or instead of molecular combing to align coded probes 130, 230, 340, 400 on a surface 100, 220, 300. Methods of performing free flow electrophoresis are known (e.g., Adjari and Prost, Proc. Natl. Acad. Sci. U.S.A. 88:4468-71, 1991). However, the present application presents the first use of free flow electrophoresis for aligning molecules on a surface.

All of the METHODS, COMPOSITIONS and APPARATUS disclosed and claimed herein can be made and used without undue experimentation in light of the present disclosure. It will be apparent to those of skill in the art that variations may be applied to the METHODS, COMPOSITIONS and APPARATUS described herein without departing from the concept, spirit and scope of the claimed subject matter. More specifically, it will be apparent that certain agents that are related may be substituted for the agents described herein while the same or similar results would be achieved. All such similar substitutes and modifications apparent to those skilled in the art are deemed to be within the spirit, scope and concept of the claimed subject matter.

What is claimed is:

1. A method comprising:
   a) obtaining two or more different coded oligonucleotide probes, each of the coded oligonucleotide probes comprising an oligonucleotide probe attached to at least one nanobarcode, wherein the nanobarcode is selected from the group consisting of carbon nanotubes, fullerenes, submicrometer metallic barcodes, nanoparticles and quantum dots;
   b) contacting a target molecule with the coded oligonucleotide probes, wherein the target molecule is a nucleic acid, and wherein the target molecule is attached to an immobilization substrate and the coded oligonucleotide probes hybridize to different locations on the nucleic acid;

c) ligating the coded oligonucleotide probes on the nucleic acid that are adjacent to one another to form ligated coded oligonucleotide probes;

d) separating the ligated coded oligonucleotide probes from the nucleic acid and non-ligated coded oligonucleotide probes;

e) aligning the ligated coded oligonucleotide probes on a surface using free flow electrophoresis; and f) identifying the ligated coded oligonucleotide probes.

2. The method of claim 1, further comprising contacting a library of coded oligonucleotide probes comprising all possible sequences for a particular length of oligonucleotide with the target molecule.

3. The method of claim 1, wherein the ligated coded oligonucleotide probes are identified by scanning probe microscopy.

4. The method of claim 3, wherein the scanning probe microscopy is selected from the group consisting of atomic force microscopy, scanning tunneling microscopy, lateral force microscopy, chemical force microscopy, magnetic force microscopy, high frequency magnetic force microscopy, electric force microscopy, scanning capacitance microscopy, scanning spreading resistance microscopy, tunneling atomic force microscopy and conductive atomic force microscopy.

5. The method of claim 1, wherein the ligated coded oligonucleotide probes aligned on the surface are identified by scanning probe microscopy.

6. The method of claim 5, further comprising determining the sequences of the coded oligonucleotide probes that hybridize to the nucleic acid.

7. The method of claim 6, further comprising determining the sequence of the nucleic acid from the sequences of the coded oligonucleotides that hybridize to the nucleic acid.

8. The method of claim 1, further comprising identifying the nucleic acid based on the coded oligonucleotide probes that hybridize to the nucleic acid.

9. A method comprising:
a) obtaining two or more coded oligonucleotide probes, each of the coded oligonucleotide probe comprising an oligonucleotide probe attached to at least one nanobarcode, wherein the nanobarcode is selected from the group consisting of carbon nanotubes, fullerenes, submicrometer metallic barcodes, nanoparticles and ciuantum dots;

b) contacting a sample comprising a nucleic acid with the coded oligonucleotide probes in a solution, and wherein the nucleic acid is attached to an immobilization substrate and the coded oligonucleotide probes hybridizes to different locations on the nucleic acid;

c) ligating the coded oligonucleotide probes on the nucleic acid that are adjacent to one another to form ligated coded oligonucleotide probes;

d) removing the nucleic acid attached to the immobilization substrate from the solution and leaving the ligated coded oligonucleotide probes in the solution;

e) subsequently, aligning the ligated coded oligonucleotide probes to a surface to form aligned ligated coded oligonucleotide probes wherein the aligned ligated coded oligonucleotide probes are arranged in an U-shape conformation;

f) identifying the ligated coded oligonucleotide probes.

10. The method of claim 9, wherein the sample further comprising two or more nucleic acids and the nucleic acids in the sample are analyzed at the same time.

11. The method of claim 9, wherein the sample further comprising two or more nucleic acids and the nucleic acids of the same type are analyzed at the same time.

12. The method of claim 9, wherein the aligned ligated coded oligonucleotide on the surface are identified by scanning probe microscopy.

13. The method of claim 12, further comprising determining sequences of the coded oligonucleotide probes that hybridize to the nucleic acid.

* * * * *

UNITED STATES PATENT AND TRADEMARK OFFICE
CERTIFICATE OF CORRECTION

PATENT NO. : 7,361,821 B2  Page 1 of 1
APPLICATION NO. : 10/251152
DATED : April 22, 2008
INVENTOR(S) : Chan et al.

It is certified that error appears in the above-identified patent and that said Letters Patent is hereby corrected as shown below:

In column 22, lines 7-8, in Claim 9, delete "ciuantum" and insert -- quantum --, therefor.

Signed and Sealed this

Fifth Day of August, 2008

JON W. DUDAS
*Director of the United States Patent and Trademark Office*